United States Patent [19]

Flora

[11] Patent Number: 5,446,382
[45] Date of Patent: Aug. 29, 1995

[54] EDDY CURRENT PROBE HAVING ONE YOKE WITHIN ANOTHER YOKE FOR INCREASED INSPECTION DEPTH, SENSITIVITY AND DISCRIMINATION

[75] Inventor: John H. Flora, Lynchburg, Va.

[73] Assignee: The Babcock & Wilcox Company, New Orleans, La.

[21] Appl. No.: 81,763

[22] Filed: Jun. 23, 1993

[51] Int. Cl.6 .................. G01R 33/12; G01N 27/90; G01N 27/82
[52] U.S. Cl. .................................... 324/232; 324/242
[58] Field of Search ............... 324/232, 238, 240, 242, 324/243, 227, 262

[56] References Cited

U.S. PATENT DOCUMENTS

| Re. 29,166 | 3/1977 | Forster | 324/37 |
|---|---|---|---|
| 2,194,229 | 3/1940 | Johnston et al. | 324/232 |
| 3,986,105 | 10/1976 | Nix et al. | 324/34 |
| 4,002,967 | 1/1977 | Fennell | 324/40 |
| 4,047,103 | 9/1977 | Day et al. | 324/34 D |
| 4,060,760 | 11/1977 | Rogachev et al. | 324/2.9 |
| 4,088,953 | 5/1978 | Sarian | 324/232 |
| 4,100,492 | 7/1978 | Forster | 324/254 |
| 4,204,159 | 5/1980 | Sarian et al. | 324/232 |
| 4,207,520 | 6/1980 | Flora et al. | 324/238 |
| 4,234,848 | 11/1980 | Diem | 324/262 |
| 4,290,016 | 9/1981 | Lorenzi | 324/216 |
| 4,379,261 | 4/1983 | Lakin | 324/240 |
| 4,397,186 | 8/1983 | Phelan et al. | 73/584 |
| 4,488,114 | 12/1984 | David et al. | 324/225 |
| 4,536,713 | 8/1985 | Davis et al. | 324/324 |
| 4,553,095 | 11/1985 | Schenk, Jr. et al. | 324/230 |
| 4,620,152 | 10/1986 | Bains, Jr. | 324/262 |
| 4,665,752 | 5/1987 | Hüschelrath et al. | 73/643 |
| 4,675,605 | 6/1987 | Watjen | 324/240 |
| 4,741,203 | 5/1988 | Willaman et al. | 73/116 |
| 4,992,735 | 2/1991 | Cullen et al. | 324/220 |

OTHER PUBLICATIONS

John Flora, "Deep Penetration Eddy Current System for Corrosion Detection and Measurement", Paper Presented in ASTM Conference Montreal, Canada, May, 1985.

John Flora, "Electromagnetic Methods for Detection of Corrosion in Steel Under Insulation" Symposium on Corrosion Under Thermal Insulation, San Antonio, Tex., Oct. 11–13, 1983.

John H. Flora, "Deep Penetration Multifrequency Eddy Current System", Qualtest Conf., Oct. 2–4, 1984, Cincinnati, Ohio.

H. L. Whaley and P. J. Latimer, "Electromagnetic/Acoustic Techniques for Inspection of Pipe Covered with Marine Growth", Materials Evaluation, vol. 59, No. 4, Apr., 1992.

John H. Flora, "Electromagnetic Methods for Detection of Corrosion in Steel Under Insulation", Contract Research Divison, Materials Technology Institute, Sep., 1983.

John H. Flora, "Deep Penetration Eddy Current Feasibility for Detection of Corrosion in Steel", Contract Research Divsion, Department of Defense, Jun. 28, 1990.

John H. Flora, "Field Feasibility of Deep Penetration Eddy Current Techniques for Detection of Corrosion Under Insulation", Contract Research Division, Materials Technology Institute, Apr., 1985.

Lixi Sales Brochure, Dec. 31, 1990.

ARCO TEMP Sales Brochure, date unknown, admitted prior art.

Primary Examiner—Walter E. Snow
Attorney, Agent, or Firm—Daniel S. Kalka; Robert J. Edwards

[57] ABSTRACT

Defects such as corrosion located on either the inner diameter or outer diameter of a covered metal component are detected through eddy current inspection. At least two concentric magnetizing yokes are held fixed with respect to each other and are scanned over the cover of the component. A magnetic flux sensor on the leg of each yoke detects changes in the magnetic flux that penetrates at different depth regions in the covered metal component, depending on the relative postion of each magnetizing yoke.

12 Claims, 4 Drawing Sheets

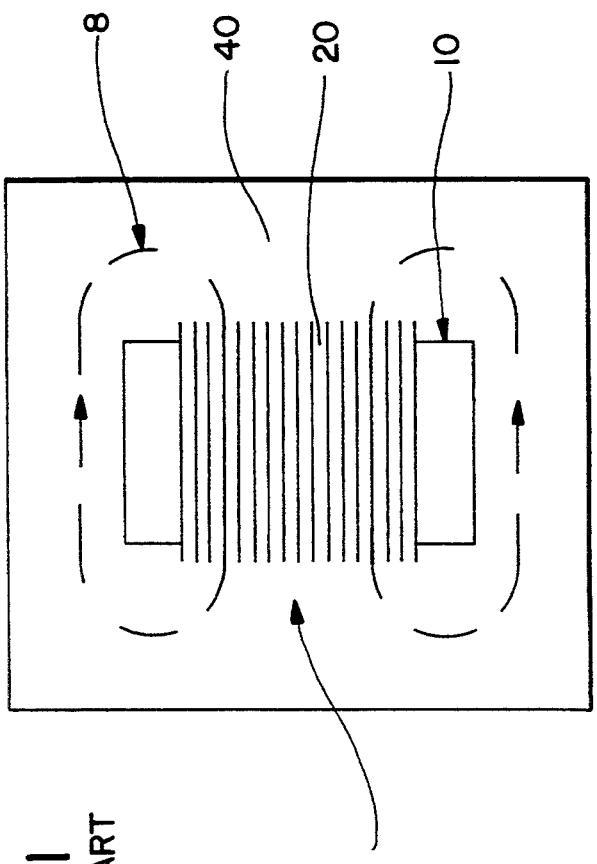
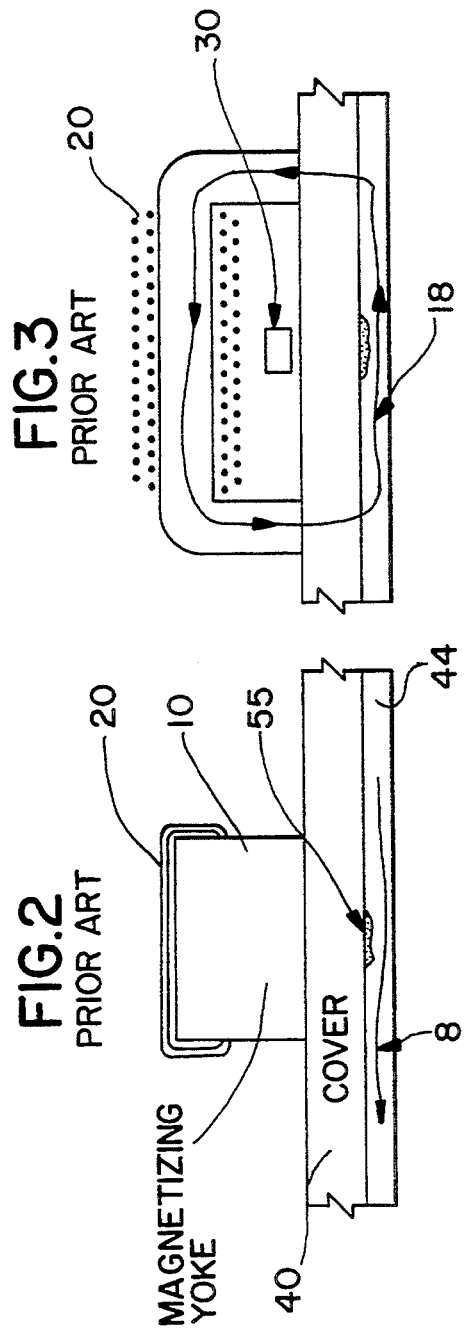

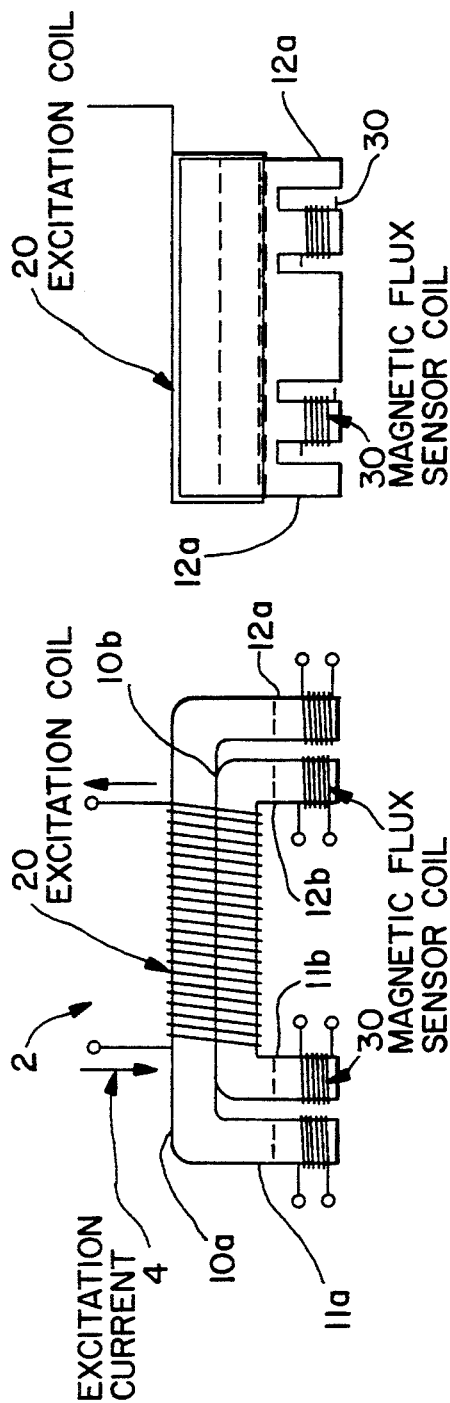
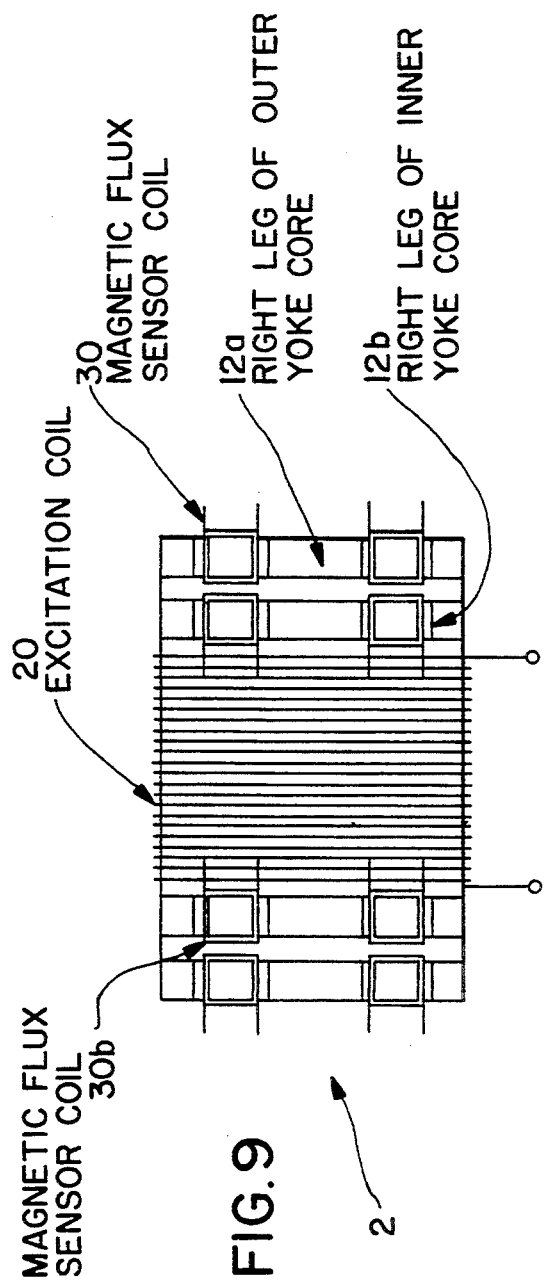

EDDY CURRENT PROBE HAVING ONE YOKE WITHIN ANOTHER YOKE FOR INCREASED INSPECTION DEPTH, SENSITIVITY AND DISCRIMINATION

BACKGROUND OF THE INVENTION

1. Field of the Invention

The present invention relates, in general, to the detection of corrosion and in particular to a new and useful method and device for the eddy current inspection of covered metal components with a design to enhance the depth of inspection by increasing the sensitivity to the magnetic fields that penetrate at the deepest depths into the component materials under inspection.

2. Description of the Related Art

Corrosion on the exterior of components such as pipes, vessels and support structures is a pervasive problem throughout the petroleum and chemical process industry costing many millions of dollars annually. A majority of these components are covered with material such as insulation which promote the corrosion by entrapment of water at the metal/cover interface. The removal of these covers and coatings for visual inspection is very costly and accounts for a substantial portion of the annual maintenance costs. Some methods have been developed in an effort to inspect covered components without removal of the insulation or covers.

However, these methods have major drawbacks. Particularly, ultrasonic inspection methods are severely limited by the need for fluid couplant, scattering of the ultrasound within the cover, air gap attenuation, mechanical alignment problems, and the poor resolution resulting from the relatively low operating frequencies required to penetrate the cover. Microwave techniques require removal of aluminum weather barriers, are adversely affected by moisture, and are scattered by insulation covers and by the shape of the corroded areas. X-radiation methods are time consuming, hazardous, relatively expensive, and are limited by the size and accessibility of the covered components.

One method developed for the inspection of pipes, tanks, and vessels through insulation is referred to as the Transient Electromagnetic Probe (TEMP). Two relevant patents have been issued; SPIES (U.S. Pat. No. 4,843,320) and Lara (U.S. Pat. No 4,843,319) This method uses the decay time of a diffusing eddy current pulse in the vessel wall to measure its thickness. The basic method is distinctly different from the low frequency eddy current (LOFEC) method in that a transient decay time of diffusing eddy current is measured rather than flux field perturbations caused by a localized defect. Other distinguishing differences are:

1. TEMP measures the average wall thickness over a large ($\geq 16$ inches diameter)—LOFEC detects the loss of surface material due to corrosion under insulation (CUI) in areas as small as 1" diameter.

2. TEMP is not a scanning technique—the very large probe head must be left in place for about 3 seconds to make a single measurement. The LOFEC method can be scanned at least as fast as 4-6"/sec (probably faster) continuously producing output signals. Therefore, the LOFEC technique can be used as an inspection, as opposed to a sampling tool.

3. There is no evidence that the TEMP method can handle the significant "artifacts" that produce signal perturbations in electromagnetic testing—these are aluminum cover overlaps, carbon steel retaining wires under the aluminum, circumferential weld beads, hidden taps or plugs, nearby support brackets, steam trace lines, etc. The LOFEC method has been designed to eliminate or minimize the effects of all those artifacts.

A second method which has been developed for the CUI problem is the portable, real-time x-ray system (LIXI®). Low energy x-rays are directed tangentially to the pipe so that they penetrate the insulation but not the pipe wall, thus imaging the corrosion area. This technique is much too slow to be used as an inspection tool to cover long lengths of pipe. The slow speed is due to a very limited field of view and the many tangential shots required to look at just one axial location on the pipe. It would be best suited to do spot checks for confirmation of corrosion damage after detection by a scanning method such as LOFEC. A second serious problem with the portable x-ray method is that scale in the corrosion site may tend to hide the corrosion damage.

In response to the deficiencies found in the methods listed above, a low frequency eddy current (LOFEC) method was developed for detecting corrosion and other defects on the surfaces of metal components that are covered with various materials such as paint, foam rubber, marine growth, calcium silicate insulation and relatively thin metal sheets. The object of the LOFEC method is to detect surface defects such as corrosion on the component while leaving the covering material intact.

FIGS. 1-5 illustrate a basic LOFEC probe generally designated 2 used for detection of surface defects such as corrosion under insulating covers. The LOFEC probe depicted in FIGS. 1-5 comprises an inverted U-shaped yoke 10 having legs 11 placed on a uniform manufactured cover 40 of a component 44 such as a steel pate. An excitation coil 20 is wound about the magnetizing yoke 10 between the legs 11. An alternating current 4 composed of one or more sinusoidal components is generated and applied to terminals 22 of the excitation coil 20. This alternating current 4 produces an alternating magnetic field 18 in the inverted U-shaped yoke 10. The yoke 10 guides the magnetic field through the cover 40 and into the component 44 beneath. If the component 44 is a ferromagnetic steel, the magnetic field 18 will be concentrated in the plate and directed from one leg of the yoke 10 toward the other. The alternating field 18 induces eddy currents 8 in the steel and other metals, (e.g., aluminum covers), located between the probe and the steel. The induced currents 8 tend to flow between and around the legs 11 of the U-shaped yoke 10 as illustrated in FIG. 1. Both the current 8 and the magnetic flux 18 are concentrated in the materials near and under the yoke 10.

FIG. 3 shows that a magnetic flux sensor 30 is located between the legs 11 of the U-shaped magnetizing yoke 10 beneath the excitation coil 20. The sensor 30 lies in a plane passing through the cross-section of the legs 11. The flux sensor 30 is an electronic device, such as a coil of conducting wire or a Hall element semiconductor that provides a signal response voltage proportional to the intensity of the magnetic flux 18 intercepted by the sensor 30 flux. Under normal conditions, e.g., a uniform steel structure with no surface defects, the magnetic flux 18 and induced eddy currents 8 in the region directly under the excitation coil windings 20 are parallel to the plane formed by the sensor 30 that intersects the legs 11. The magnetic flux 18 flows from one leg 11 to the other and induced current 8 flows perpendicular to the flux 18. The presence of a near surface defect 55 in the steel component 44, such as corrosion, causes a change in the magnitude, phase and direction of the induced currents 8 and associated magnetic field 18 within the steel 44 and in the region between the steel 44 and the probe 2.

Surface defects 55 are identified by scanning the probe 2 over the cover 40 of the structure 44 and detecting the signal response voltage, observed at terminals 33 of the flux sensor 30.

U.S. patent application Ser. No. 07/973,515 filed Nov. 9, 1992 discloses a method and device for reducing or minimizing extraneous and unwanted signal responses caused by variations in the geometry and electromagnetic properties of the component 44 when using the LOFEC technique.

That device can detect defects on metal components covered with marine growth while minimizing extraneous signal responses.

Also, U.S. patent application Ser. No. 07/973,516 filed Nov. 9, 1992 relates to a device and method directed to a similar purpose.

Other patents relating to eddy current inspection techniques include U.S. Pat. Nos. 4,207,520; 4,488,114; 4,553,095; and 4,379,261.

A need still remains for a method or device that can enhance the depth of inspection by increasing the sensitivity to the magnetic fields that penetrate at the deepest depths into the component materials under inspection. Also, a need exists for inspecting the inner diameter (ID) surfaces of a pipe without removing insulation particularly when corrosion can occur where corrosive liquids are being processed.

SUMMARY OF THE INVENTION

The present invention solves the aforementioned problems with the prior art as well as others by providing an eddy current probe with a core having at least two sections or yokes to implement approximate concentric paths for the interrogating magnetic flux. The corresponding legs of the yokes are separated by a predetermined distance with sensing coils being wound around the legs.

One object of the present invention is to provide an eddy current probe which is designed to enhance the depth of penetration.

Another object of the present invention is to provide an eddy current probe which can detect and quantify the extent of corrosion on either the inner diameter (ID) or outer diameter (OD) surfaces of a pipe without removing insulation.

Still another object of the present invention is to provide a method and device for inspecting either the ID or OD surfaces of a pipe without removing insulation.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiments of the invention are illustrated.

BRIEF DESCRIPTION OF THE DRAWINGS

In the drawings:

FIG. 1 is a top view of a known probe for a low frequency eddy current system;

FIG. 2 is a side view of the probe of FIG. 1;

FIG. 3 is a cross-sectional front view of the probe of FIG. 1;

FIG. 8 is a cross-sectional elevated front view of a second embodiment of the present invention;

FIG. 9 is a bottom view of the present invention according to FIG. 8; and

FIG. 10 is an end view of still another embodiment of the present invention.

DESCRIPTION OF THE PREFERRED EMBODIMENTS

Figure 4:
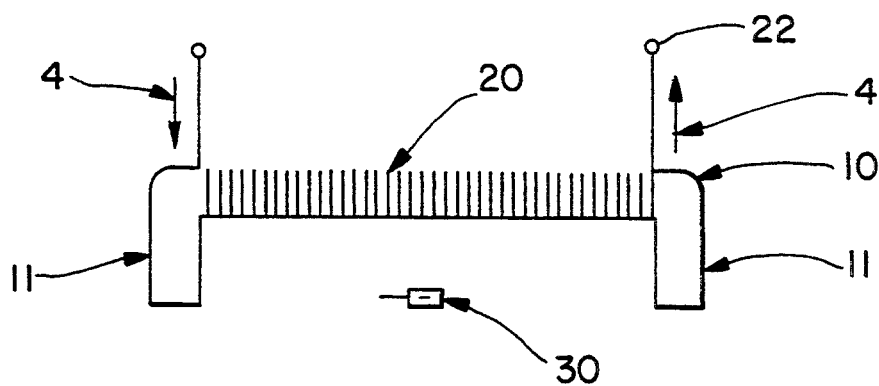
FIG. 4 is a partial front view of the probe of FIG. 1.
Figure 5:
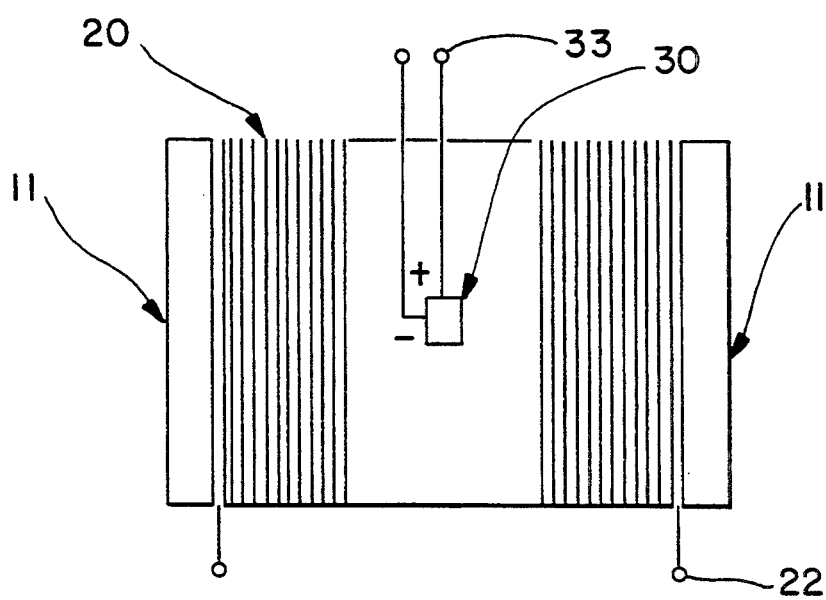
FIG. 5 is a bottom view of the probe of FIG. 1.
Figure 6:
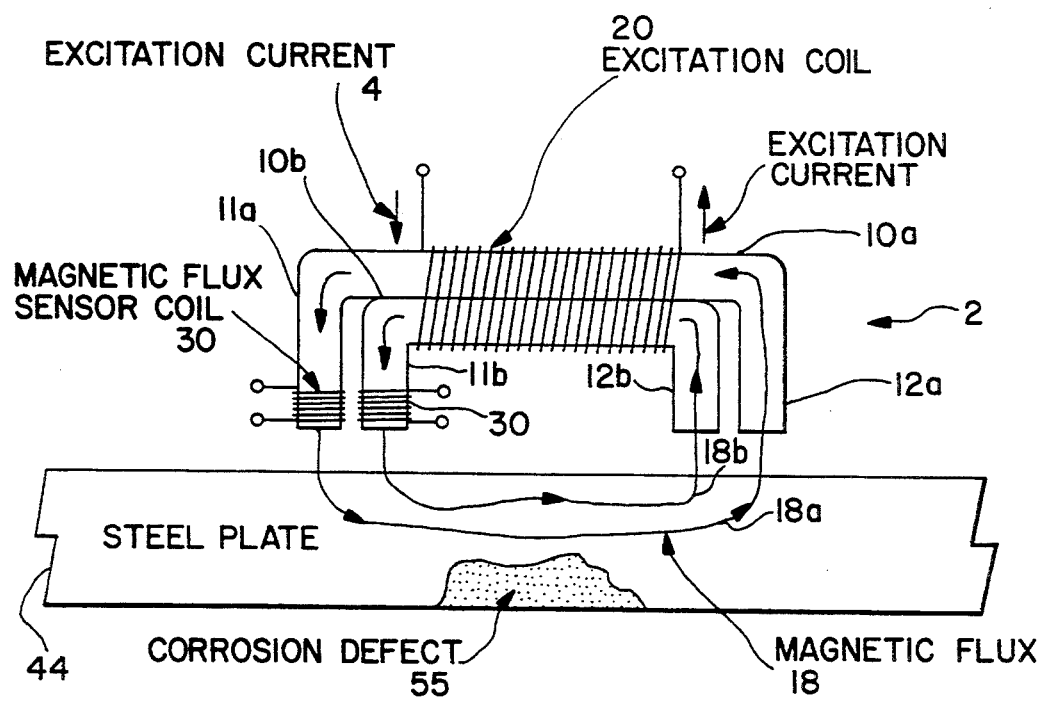
FIG. 6 is a cross-sectional elevated front view of a probe of the present invention.
Figure 7:
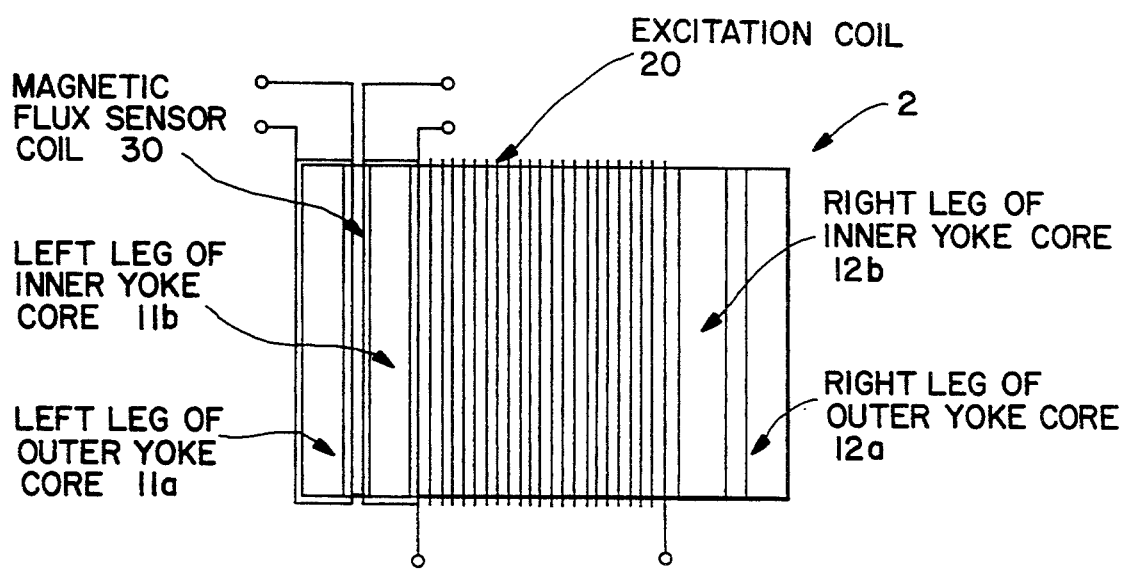
FIG. 7 is a bottom view of the present invention shown in FIG. 6.

Referring to the figures, where like numerals designate like or similar features throughout the several views, and particularly to FIGS. 6–9, the present invention employs an eddy current probe 2 composed of two or more ferromagnetic yokes 10a,b to implement approximate concentric paths for the interrogating magnetic flux. Two U-shaped magnetizing yokes 10a,b are constructed and assembled so that the smaller yoke 10b fits inside the larger yoke 10a with the upper parts making physical contact, but with the corresponding legs 11a,b of the yokes 10a,b separated by a relatively small predetermined distance. One excitation coil 20 is wound around the upper parts of both magnetizing yokes 10a,b as shown in FIGS. 6–9. Sensing coils 30 are wound around legs 11a,b of the magnetizing yokes 10a,b. Magnetic flux sensors 30, such as Hall elements, can be installed on the ends of the legs 11a,b or internal to the legs in place of the sensing coils wound around the legs.

Application of an alternating current 4 to the excitation coil 20 generates a magnetic field 18 and corresponding magnetic flux in both of the U-shaped yokes 10a,b. When the excitation coil current 4 is positive, the flux 18 will exit the left legs 11a,b and enter the right legs 12a,b. This order is reversed as the excitation current 4 changes from positive to negative. Part of the magnetic flux 18 penetrates the test component material 44. If the material is ferromagnetic and has a relatively high magnetic permeability, e.g. carbon steel, then the magnetic flux 18 is drawn into the component 44 and enters or exits in a direction that is nearly perpendicular to the component surface. It is well-known that the flux lines 18a,b from the two yokes 10a,b will not intersect. Therefore, the flux 18b generated by the inner yoke 10b effectively pushes the flux 18a that is generated by the outer yoke 10a deeper into the test component 44. Consequently, there is a significantly greater change in the magnetic flux 18a in the outer yoke 10a caused by a defect such as the corroded area 55 on the far side of the component 44 i.e. on the side opposite the probe.

Since the sensor 30 on the legs 11a, 12a of the outer yoke 10a detects only the changes in the deep penetrating magnetic flux 18a, signal responses to defects on the far surface are increased while the signal responses to defects on the near surface are decreased. The outer yoke sensor 30a is also less sensitive to near surface variables such as local changes in magnetic permeability and electrical conductivity in the volume of test components nearest the eddy probe. In other words, the signal-to-noise ratio achieved by the sensor on the outer yoke 10a is improved by the magnetic flux 18b generated by the inner yoke 10b.

Similarly, the sensor 30 on the leg 11b of the inner yoke 10b will detect only the changes in the shallow magnetic flux 18b i.e. the magnetic flux nearest the probe-side surface of the test component. Consequently, the inner yoke sensor is more sensitive to near surface defects, variations in magnetic permeability and variations in electrical conductivity in the volume of test component material nearest the surface. This provides the additional capability of identification of defects as to their location on either the near (O.D.) or far surfaces (I.D.) of the component 44.

The signal response to near surface variables is further reduced by applying a multifrequency current to the excitation coil. For example, an excitation current containing two frequencies is used to generate an alternating magnetic flux having the same frequency components. The lower frequency signal response is extracted from the outer yoke sensors and the higher frequency signal response is extracted from the inner yoke sensors. The high frequency signal response is then subtracted from the low frequency signal response with known electrical signal processing equipment to reduce the amplitude of signals caused by the unwanted near-surface variables.

A second embodiment accommodates two or more sensor coils on each leg 11, 12 as shown in FIGS. 8 and 9. Two or more pairs of coils 30 on each leg can be differentially connected, i.e. connected in series with opposing polarity. This provides a means of reducing the signal responses to variations in test component properties, structure and geometry that one encounters as the probe is scanned over the surface of the material. For example, the signal response that occurs as the probe is scanned over a circumferential weld in a steel pipe will be reduced by the differentially connected coils. However, the signal response to localized areas of corrosion is not diminished to an appreciable extent by the differential connection so that an improvement in the signal-to-noise ratio is realized.

As is immediately apparent, the invention is expandable to include more than two concentric yokes 10a,b . . . or magnetic circuits with each leg of the yoke having one or more magnetic flux sensors. Corresponding sensors on the right and left legs of the same yoke section can be connected in either series aiding or opposing. Also each leg of a given yoke can contain two or more each of sensors connected in series aiding or opposing. The pairs of sensors 30 can be connected in all possible combinations. Similarly, there may be at least two legs to each side of each yoke as seen in FIG. 10.

The present invention provides a means of increasing the penetration depth of the magnetic flux and associated eddy currents in component structures that are being inspected or processed by the eddy current technique. It provides a means of increasing the sensitivity, i.e. signal-to-noise ratio, to defects internal to the thickness of the test component or on the surface of the test component that is farthest from the eddy current probe. Signal responses from the outer magnetic circuit or yoke provide a means of identifying and characterizing defects on the far surface of the test component and signal response from the inner magnetic yoke provides a means of identifying and characterizing defects on the near surface of the test component.

While specific embodiments of the present invention have been shown and described in detail to illustrate the application of the principle of the present invention, it will be understood that the invention may be embodied otherwise without departing from such principles.

What is claimed is:

1. A device for detecting a defect on a metal component having a cover, the device comprising:

two magnetizing yokes, each yoke having a body supported by at least two legs for contacting the cover and supporting the body over the cover thereby maintaining the yoke in a fixed orientation with respect to the metal component, one of said yokes being smaller in size than said other yoke and constructed to fit inside said other yoke with an upper part of each yoke making physical contact while said legs of the two yokes are separated by a predetermined distance;

an excitation coil wound around the bodies of the two yokes between the legs for receiving an alternating current and producing separate alternating magnetic fields through the yokes and corresponding magnetic flux in each yoke with one magnetic flux pushing the other magnetic flux into the metal component; and magnetic flux sensor means for each yoke for scanning for changes in the magnetic flux from each yoke for detecting a defect.

2. The device according to claim 1, wherein each magnetizing yoke has a plurality of legs.

3. The device according to claim 1, wherein said magnetic flux sensor means comprises a magnetic flux sensor coil attached to at least one leg of each yoke.

4. The device according to claim 3, wherein said at least one leg of each yoke is on the same side of each yoke.

5. The device according to claim 3, wherein said at least one leg of each yoke is on opposite sides.

6. The device according to claim 1, wherein said magnetic flux sensor means comprises at least one magnetic flux sensor positioned in an area underneath each yoke.

7. The device according to claim 3, wherein said magnetic flux sensor coils are differentially connected with respect to each other.

8. The device according to claim 3, wherein said magnetic flux sensor coils are attached to every leg of each yoke.

9. A method of detecting a defect on a metal component having a cover, the method comprising the steps of:

winding an excitation coil around two magnetic yokes;

positioning one yoke inside the other yoke so that an upper part of each yoke makes physical contact while the legs of the yokes are separated by a predetermined distance;

placing the two yokes of ferromagnetic material on the cover over the component;

applying an alternating current to the excitation coil for producing an alternating magnetic field through each yoke and corresponding magnetic flux in each yoke with one magnetic flux pushing the other magnetic flux into the metal component;

moving the two yokes along the cover of the component thereby scanning for defects; and monitoring each alternating magnetic field and each magnetic flux using magnetic flux sensor means for detecting changes which is indicative of defects in the component.

10. The method according to claim 9, wherein a plurality of pairs of magnetic flux sensors are differentially connected with respect to each other.

11. The method according to claim 10, wherein the plurality of magnetic flux sensors are oriented on at least one leg of each yoke.

12. The method according to claim 9, wherein the magnetic flux sensor means includes a magnetic flux sensor placed in the area between the excitation coil and the cover of the component.

* * * * *